United States Patent [19]

Staples et al.

[11] Patent Number: 6,159,698
[45] Date of Patent: *Dec. 12, 2000

[54] REAGENTS FOR ASSAYS FOR MYCOPHENOLIC ACID

[75] Inventors: Mark A. Staples; Richard F. Parrish, both of San Jose, Calif.

[73] Assignee: Dade Behring Marburg GmbH, Marburg, Germany

[*] Notice: This patent is subject to a terminal disclaimer.

[21] Appl. No.: 08/895,856

[22] Filed: Jul. 17, 1997

Related U.S. Application Data

[60] Provisional application No. 60/022,120, Sep. 18, 1996.

[51] Int. Cl.$^7$ .................. G01N 33/53; G01N 33/531; G01N 33/543; G01N 1/00
[52] U.S. Cl. .................. 435/7.1; 435/7.92; 435/7.9; 435/961; 435/975; 436/518; 436/548; 436/174; 436/825
[58] Field of Search .................. 435/7.1, 7.92, 435/7.9, 961, 962, 975; 436/518, 548, 174, 825

[56] References Cited

U.S. PATENT DOCUMENTS

| | | | |
|---|---|---|---|
| 3,817,837 | 6/1974 | Rubenstein et al. | 195/103.5 |
| 3,996,345 | 12/1976 | Ullman et al. | 424/12 |
| 4,052,504 | 10/1977 | Hertl et al. | 424/1 |
| 4,110,076 | 8/1978 | Margherita | 23/230.6 |
| 4,199,483 | 4/1980 | Jones | 252/559 |
| 4,233,402 | 11/1980 | Maggio et al. | 435/7 |
| 4,275,149 | 6/1981 | Litman et al. | 435/7 |
| 4,299,916 | 11/1981 | Litman et al. | 435/6 |
| 4,318,980 | 3/1982 | Boguslaski et al. | 435/7 |
| 4,332,786 | 6/1982 | Cabelli et al. | 424/1 |
| 4,366,143 | 12/1982 | Midgley et al. | 436/501 |
| 4,451,571 | 5/1984 | Allant | 436/505 |
| 4,454,232 | 6/1984 | Breglio et al. | 436/504 |
| 4,468,469 | 8/1984 | Atkinson et al. | 436/500 |
| 4,486,530 | 12/1984 | David et al. | 435/7 |
| 4,559,291 | 12/1985 | Neumann et al. | 430/214 |
| 4,798,804 | 1/1989 | Khanna et al. | 436/94 |
| 4,857,453 | 8/1989 | Ullman et al. | 435/7 |
| 4,868,104 | 9/1989 | Kurn et al. | 435/6 |
| 4,959,303 | 9/1990 | Milburn et al. | 435/7 |
| 5,063,165 | 11/1991 | Hu et al. | 436/500 |
| 5,089,390 | 2/1992 | Davalian et al. | 435/7.93 |
| 5,185,243 | 2/1993 | Ullman et al. | 435/6 |
| 5,278,080 | 1/1994 | Midgley et al. | 436/500 |
| 5,378,636 | 1/1995 | Hu et al. | 436/500 |

FOREIGN PATENT DOCUMENTS

| | | |
|---|---|---|
| 2014233 | 10/1990 | Canada . |
| 0 100 543 | 2/1984 | European Pat. Off. . |
| 0 155 104 | 9/1985 | European Pat. Off. . |
| 0 165 669 | 12/1985 | European Pat. Off. . |
| 0 218 309 | 4/1987 | European Pat. Off. . |
| 0 392 332 | 10/1990 | European Pat. Off. . |
| 0565949 | 10/1993 | European Pat. Off. . |
| 8187-862 | 11/1983 | Japan . |
| 2085160 | 4/1982 | United Kingdom . |
| 83/00147 | 1/1983 | WIPO . |
| WO 83/00147 | 1/1983 | WIPO . |
| 96/02004 | 1/1996 | WIPO . |

OTHER PUBLICATIONS

Nishijo et al. Chem. Pharm. Bull. 33: 2648–2653, 1985.
Basak. Asian J. Chem. 5(2):316–318, 1993.
Broughton and Strong, *Clin. Chem.* 22:726–732 (1976).
Butler, *J. Immunol. Meth.* 7:1–24 (1975).
Cuatrecasas, *J. Biol. Chem.* 245:3059 (1970).
Epinette, et al., *Journal of the American Academy of Dermatology* 17(6):962–71 (1987).
Galfre, et al. (1981) Preparation of monoclonal antibodies: strategies and procedures, *Methods Enzymol.* 73:3–46.
Grabarek, et al., (1990) Zero–length crosslinking procedure with the use of active esters, *Anal. Biochem.* 185:131–135.
Köhler and Milstein, *Nature* 265:495–497, 1975.
Langman, et al., *Therapeutic Drug Monitoring* (1994) 16:602–607.
Lee, et al., *Pharmaceutical Research* 7(2):161–166 (1990).
Lymphocyte Hybridomas, ed. Melchers, et al. Springer–Verlag (New York 1978).
Nature 266:495 (1977).
Nelson, et al., *Journal of Medicinal Chemistry* 33(2):833–838 (1990).
Playfair, et al., *Br. Med. Bull.* 30:24–31 (1974).
Science 208:693 (1980).
Yalow, et al., *J. Clin. Invest.* 39:1157 (1960).
Basak, D., Interaction of Transition Metal Ions with some Biologically Active Ligands, *Asian Journal of Chemistry*, vol. 5, No. 2 (1993), 316–318.
Shaw, et al., Mycophenolic Acid: Measurement and Relationship to Pharmacologic Effects, *Therapeutic Drug Monitoring*, vol. 17, No. 16, pp. 685–689, 1995.
Erre, L., et al. Interaction of Metal Ions With Humic–Like Models–X. Synthesis, Spectral Properties and Thermal Decomposition of Copper (II) Methoxy– And Dimethoxy–Benzoates, *Polyhedron*, vol. 6, No. 10, pp. 1869–1874, 1987.
Pethe, L.D., et al., A Simple Continuous Titration Technique for Determining pK Values of Protonated Ligands, *Indian Journal of Chemistry*, vol. 15A, Nov., 1977, pp. 998–1001.

(List continued on next page.)

*Primary Examiner*—James C. Housel
*Assistant Examiner*—S. Devi
*Attorney, Agent, or Firm*—Cara Z Lowen; Linda M Buckley

[57] ABSTRACT

One aspect of the present invention relates to assays for the detection of mycophenolic acid. The method comprises including in an assay medium suspected of containing mycophenolic acid a releasing agent for releasing mycophenolic acid from a complex with endogenous proteins. Another aspect of the present invention is an improvement in a method for the determination of mycophenolic acid in a sample suspected of containing such analyte. The method comprises the steps of (a) providing in combination in an assay medium the sample and a binding partner for the analyte and (b) detecting the binding of the binding partner to the analyte. The improvement comprises including in the assay medium a releasing agent for releasing mycophenolic acid from a complex with endogenous proteins. The present invention also provides assay reagents as well as packaged kits useful for performing the methods of the invention.

28 Claims, No Drawings

OTHER PUBLICATIONS

Lucanska, B., et al., Thermal Analysis of some Copper p–methoxybenzoate complexes, *Zb. Celostatnej Konf. Term. Anal.*, $8^{th}$ (1979) 255–8, Abstract.

Carey, "Organic Chemistry", McGraw Hill, Inc., NY NY, $1^{st}$ ed., 1987, pp. 609 & 994–995.

Heathcock, et al., "Introduction to Organic Chemistry", MacMillan Pub Co., NY NY, $3^{rd}$ ed, 1985 pp. 493 & 814.

Nerli et al., *Arch Int Physiol Biochim Biophys* (1994) 102(1): 5–8.

Seth et al., *Clin Chem* (1975) 21 (10): 1406–1413.

Wu, J.C., *Perspectives in Drug Discovery and Design*, 2 (1994) p. 185–204.

Allison et al., "Mechanisms of Action of Mycophenolic Acid," Annals of New York Academy of Science, vol. 696, pp. 63–87, 1993.

Haley et al., "Analytical Performance of an Emil® Assay for Mycophenolic Acid in Plasma," Clinical Chemistry, 43(6):S209 Abstract No. 474, Jun. 1997.

Holt et al., "Monitoring New Immunosuppasive Agents: Are the Methods Adequate?" Drug Metabol. Drug Inter. 14(1): 5–15, 1997.

Langman et al., "Blood Distribution of Mycophenolic Acid," Therapeutic Drug Monitoring, 16: 602–607, Dec. 1994.

Nowak et al., "Mycophenolic Acid Binding to Human Serum Albumin: Characterization and Relations to Pharmacodynamics," Clin. Chem. 41(7): 1011–1017, 1995.

Shaw et al., "Mycophenolic Acid: Measurement and Relationship to Pharmacologic Effects," Therap. Drug Monitoring 17: 685–689, 1995.

Tsina et al., "High–Performance Liquid Chromatographic Method for the Determination of Mycophenolate Mofetel . . . " J. Chromatog. B 681: 347–353, Jun. 1996.

Yatscoff et al, "Pharmacodynamic Monitoring of Immunosuppressive Drugs," Transplantation Proceedings, 28(6): 3013–3015, Dec. 1996.

REAGENTS FOR ASSAYS FOR MYCOPHENOLIC ACID

This application claims the benefit of U.S. Provisional Application Ser. No. 60/022,120, filed Sep. 18, 1996.

BACKGROUND OF THE INVENTION

1. Field of the Invention

Mycophenolic acid ("MPA") is produced by the fermentation of several penicillium species. It has a broad spectrum of activities, specific mode of action, and is tolerable in large doses with minimal side effects, Epinette, et al., *Journal of the American Academy of Dermatololqy* 17(6):962–71 (1987). MPA has been shown to have antitumor, antiviral, antipsoriatic, immunosuppressive, anti-inflammatory activities, Lee, et al., *Pharmaceutical Research* 7(2):161–166 (1990), along with antibacterial and antifungal activities, Nelson, et al., *Journal of Medicinal Chemistry* 33(2):833–838 (1990). It inhibits inosine monophosphate dehydrogenase, an enzyme in the de novo synthesis of purine nucleotides. Since T and B lymphocytes depend largely upon this de novo synthesis, MPA is able to inhibit lymphocyte proliferation, which is a major factor of the immune response.

The morpholinoethyl ester of MPA, morpholinoethyl (E)-6-(1,3-dihydro4-hydroxy-6-methoxy-7-methyl-3-oxo-5-isobenzofuranyl)-4-methyl-4-hexenoate ("MPA-M") is rapidly hydrolyzed in vivo to MPA. Administration of MPA in the form of this ester, greatly improves MPA's bioavailability.

Because MPA is a potent biologically active material, an effective immunoassay could be useful in monitoring its bioavailability. In addition, it may be important to monitor therapeutic drug levels, i.e., optimal drug levels necessary for adequate immunosuppression. Since MPA-M is rapidly hydrolyzed to MPA, an assay for MPA would provide means of regulating and optimizing MPA-M dosages.

MPA levels in patient samples have been determined by high performance liquid chromatography (HPLC). Prior to conducting the HPLC analysis, the sample to be determined was subjected to solid phase extraction using organic solvent elution or direct organic solvent extraction.

2. Description of the Related Art

Nowak, et al., *Clin. Chem.* (1995) 41(7): 1011–1017 discusses mycophenolic acid binding to human serum albumin: characterization and relation to pharmacodynamics.

Langman, et al., *Therapeutic Drug Monitoring* (1994) 16:802–807 discusses blood distribution of mycophenolic acid.

European Patent 0 218 309 B1 discloses a method for measuring free ligands in biological fluids. Sodium salicylate and 2,4-dinitrophenol were employed to prevent labeled analogs of triiodothyronine and tetraiodothyronine from binding to albumin and thyroid binding pre-albumin.

European Patent Application 0 392 332 A2 discloses a fluorescent polarization immunoassay and reagents therefor. Various compounds were disclosed for converting a marijuana metabolite, which was bound to serum albumin and other proteins in urine, to free form. These compounds included, among others, 8-anilino-1-naphthalenesulfonic acid (ANS), salicylic acid and 5-methoxysalicylic acid.

SUMMARY OF THE INVENTION

One aspect of the present invention is a method for releasing bound mycophenolic acid from a complex of mycophenolic acid and proteins. A medium suspected of containing the complex is combined with a releasing agent in an amount effective to release the mycophenolic acid from the complex.

Another aspect of the present invention is an assay method for measuring the total amount of mycophenolic acid in a sample suspected of containing mycophenolic acid and endogenous proteins that bind to the mycophenolic acid. In the method the sample, assay reagents for measuring the amount of the mycophenolic acid, and a releasing agent in an amount effective to release the mycophenolic acid from a complex thereof with endogenous proteins are combined in a medium. The amount of the mycophenolic acid is determined by means of the assay reagents.

Another aspect of the present invention is an improvement in a method for the determination of mycophenolic acid in a sample suspected of containing mycophenolic acid. The method comprises the steps of (a) providing in combination in an assay medium the sample and a binding partner for mycophenolic acid and (b) detecting the binding of the binding partner to the mycophenolic acid. The improvement comprises including in the assay medium a releasing agent in an amount effective to release mycophenolic acid from a complex thereof with endogenous proteins.

Another embodiment of the present invention is an improvement in the above method for the determination of mycophenolic acid in a sample suspected of containing mycophenolic acid wherein the releasing agent is an anisic acid or 8-anilino-1-naphthalene sulfonic acid.

Another embodiment of the present invention is a method for measuring the amount of mycophenolic acid in a sample suspected of containing mycophenolic acid and endogenous proteins that bind to said mycophenolic acid. The method comprises (a) combining in an aqueous medium (i) sample, mycophenolic acid conjugated to a detectable label, and (iii) an antibody capable of binding to mycophenolic acid, and (b)-determining the effect of said sample on the activity of said label. The improvement comprises including in the medium a releasing agent in an amount effective to release the mycophenolic acid from a complex thereof with endogenous proteins.

Another aspect of the present invention is a kit for conducting an assay for the determination of mycophenolic acid. The kit comprises in packaged combination (a) an antibody capable of binding to mycophenolic acid, (b) a compound comprising mycophenolic acid bound to a detectable label, and (c) an effective amount of a releasing agent.

DESCRIPTION OF THE SPECIFIC EMBODIMENTS

It is known that MPA is highly protein-bound in plasma (83→98%). It is also known that patient blood samples to be analyzed contain a number of proteins such as, e.g., albumin. Despite this high level of protein binding of MPA, we initially found that a dose-response curve could be obtained when samples suspected of containing MPA were subjected to assay methods such as immunoassay methods and the like. Accordingly, there was no need for releasing MPA from bound protein for conducting an immunoassay for the determination of MPA in patient samples. It appeared that one average protein concentration for calibrators could be employed representing all patient samples. Additionally, binding of molecules to albumin typically is on the order of about $10^6$ M whereas the binding of antibodies to their respective cognates is on the order of about $10^9$ M. Thus, the expectation was that the stronger antibody binding would prevail over the weaker binding to albumin.

Surprisingly, however, we discovered that immunoassays conducted on samples from some patients undergoing treatment with MPA gave discrepant results. Upon investigation, we discovered that some patients had very low blood protein concentrations, which resulted in over quantitation in the analysis of samples from such patients using the above calibrators.

Furthermore, patients under treatment with MPA and cyclosporin or tacrolimus may be co-administered numerous drugs including, but not limited to, azathioprine, prednisone, methylprednisolone, antivirals, antibiotics, antifungals, cardiovascular agents, diabetic agents and diuretic agents. Many of these drugs have profound effects on metabolism and result in changes in concentrations of various serum/plasma components. Also, some drugs, for example, salicylate and some of the above drugs, are known to cause an increase in the MPA free fraction when salicylate was added at concentrations that may be observed in patients (see, e.g., Nowak, supra). There exists, therefore, the potential for interference by these components, either directly or indirectly, in the determination of MPA in the target patient population.

Before proceeding with the description of the specific embodiments of the invention, a number of terms will be defined.

Mycophenolate ester—includes, but is not limited to, esters of MPA at the carboxylic acid group of the side chain attached at the 1'-position of the MPA isobenzofuranyl ring system such as MPA-M.

MPA metabolite—a product of the metabolism of MPA, preferably a product containing the isobenzofuranyl ring system, more preferably products also containing a portion of the side chain such as the acyl or phenolic glucuronide of MPA.

Measuring the amount of MPA—quantitative, semiquantitative, and qualitative methods as well as all other methods for determining MPA are considered to be methods of measuring the amount of MPA. For example, a method which merely detects the presence or absence of MPA in a sample suspected of containing MPA is considered to be included within the scope of the present invention. The terms "detecting" and "determining", as well as other common synonyms for measuring, are contemplated within the scope of the present invention.

Sample suspected of containing MPA—usually biological tissue including excised tissue from an organ or other body part of a host and body fluids, for example, urine, whole blood, plasma, serum, saliva, semen, stool, sputum, cerebral spinal fluid, tears, mucus, and the like. Preferably, the sample is plasma or serum.

Capable of distinguishing between—the ability of a receptor or antibody to bind preferentially to a first ligand relative to a second ligand. Usually at least 5-fold more of the first ligand than the second ligand will be bound when the antibody is combined with a sample containing the ligands. Preferably, at least 10-fold more and, more preferably, at least 20-fold more of the first ligand will be bound. Although the relative binding of each ligand will depend on the relative concentrations in the sample, usually these conditions are met when the binding constant of the antibody to the first ligand is at least equal to the binding constant to the second ligand, and preferably, is at least 10-fold, more preferably, at least 50-fold the binding constant to the second ligand. The crossreactivity of an antibody to a first ligand refers to the ratio of the concentration of the first ligand to that of the second ligand that causes the two ligands to be bound in equal amounts. Quantification of a "high" or "low" degree of cross-reactivity, i.e., the extent of cross-reactivity that is acceptable, depends on the highest concentration expected of the cross-reactant, the sensitivity required for the assay and the accuracy needed. For example, if an antibody is 10% cross-reactive with MPA-G and MPA-G is present in a sample in an amount five times greater than the lowest level of MPA to be detected, then the measured level of MPA will be 50% too high when MPA is at its lowest level. If only a 5% error is acceptable, then the cross-reactivity would have to be less than 1%.

Conjugate—a molecule comprised of two or more molecules bound together, optionally through a linking group, to form a single structure. The binding can be made either by a direct connection (e.g. a chemical bond) between the molecules or by use of a linking group. For example, an MPA analog conjugated to an enzyme is an MPA analog-enzyme conjugate.

Linking Group—a portion of a structure which connects 2 or more substructures. The linking group can be a bond or it can have at least 1 uninterrupted chain of atoms other than hydrogen (or other monovalent atoms) extending between the substructures. The number of atoms in the chain will be at least one and is determined by counting the number of atoms other than hydrogen along the shortest route between the substructures being connected, and is typically 1–30, usually 2–10, preferably 3–8, atoms each independently selected from the group consisting of carbon, oxygen, nitrogen, sulfur and phosphorous. The number of total atoms in the linking group is determined by counting the total carbon, oxygen, nitrogen, sulfur and phosphorous atoms, i.e. the atoms other than hydrogen. Typically, the linking group has a total of less than 30 atoms, preferably less than 20 atoms, more preferably less than 10 atoms. As a general rule, the length of a particular linking group can be selected arbitrarily to provide for convenience of synthesis and the incorporation of any desired group. The linking groups may be aliphatic or aromatic, although with diazo groups, aromatic groups will usually be involved. Oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, dithiol, ether, urea, thiourea, guanidine, azo, thioether and carboxylate, sulfonate, and phosphate esters, amides and thioesters.

MPA analog—a modified MPA, which can compete with the analogous MPA for a receptor, the modification providing means to join MPA to another molecule. The MPA analog will usually differ from the MPA by more than replacement of a hydrogen with a bond which links the MPA analog to a hub or label, but need not. The MPA analog can bind to the receptor in a manner similar to the MPA. The analog could be, for example, an antibody directed against the idiotype of an antibody to MPA.

Member of a specific binding pair ("sbp" member)—one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. Complementary sbp members bind to one another, as for example, a ligand and its complementary receptor. With respect to two complementary sbp members, one may be referred to as the "binding partner" for the other. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Small molecules are often covalently bound to other sbp members to form a conjugate having at least one, and frequently 2–20, small molecules. Bonding of the small molecule to the sbp member may be accomplished by chemical reactions which result in replacing a hydrogen atom of the small molecule with a bond to the sbp member or by a linking group between the small molecule and the sbp member of any size but preferably no larger than necessary to permit binding to the conjugate of both a receptor for the small molecule and the sbp member.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Non-specific complex of MPA—MPA bound non-specifically to another substance, usually, endogenous substances present in a sample to be analyzed. The endogenous substances generally are endogenous proteins such as plasma proteins, e.g., albumin, globulins, glycoproteins, lipoproteins, and the like.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) (see, e.g., Parker, Radioimmunoassay of Biologically Active Compounds, Prentice-Hall (Englewood Cliffs, N.J., U.S., 1976), Butler, J. Immunol. Meth. 7:1–24 (1975); Broughton and Strong, Clin. Chem. 22: 726–732 (1976); and Playfair, et al., Br. Med. Bull. 30: 24–31 (1974)) or by preparing continuous hybrid cell lines and collecting the secreted protein (monoclonal) (see, e.g., Köhler and Milstein, Nature 265:495–497, 1975, Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981)) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Hapten—a compound capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier. Haptens are a subset of ligands.

Immunogenic carrier—a group which, when conjugated to a hapten and injected into a mammal, will induce an immune response and elicit the production of antibodies that bind to the hapten, in this case MPA. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Other suitable immunogenic carriers include albumins, serum proteins, e.g., globulins, ocular lens proteins and lipoproteins. Illustrative proteins include bovine serum albumin, keyhole limpet hemocyanin ("KLH"), ovalbumin and bovine gamma-globulin.

Support or surface—a solid phase, typically a support or surface, which is a porous or non-porous water insoluble material that can have any one of a number of shapes, such as strip, rod, plate, well, particle and bead. A wide variety of suitable supports are disclosed in Ullman, et al. U.S. Pat. No. 5,185,243, columns 10–11, Kurn, et al., U.S. Pat. No. 4,868,104, column 6, lines 21–42 and Milbum, et al., U.S. Pat. No. 4,959,303, column 6, lines 14–31, which are incorporated herein by reference. Binding of sbp members to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). As used herein, the term "capable of being bound to a support" means, for example, that a reagent, such as the anti-analyte antibody, is bound to a first sbp member or a small molecule and a complementary second sbp member or receptor for the small molecule, is in turn bound a support. Alternately, a receptor for the anti-analyte antibody, such as an anti-mouse antibody, is bound to a support and used to capture the anti-analyte antibody. Therefore, the antianalyte antibody is not actually bound to a support, but will become bound, when a complementary sbp member or receptor is added.

Signal producing system ("sps")—one or more components, at least one component being a detectable label, which generate a detectable signal that relates to the amount of bound and/or unbound label, i.e. the amount of label bound or not bound to the compound being detected.

The label is any molecule that produces or can be induced to produce a signal, and preferably is a fluorescer, radiolabel, enzyme, chemiluminescer or photosensitizer. Thus, the signal is detected and/or measured by detecting fluorescence or luminescence, radioactivity, enzyme activity or light absorbance.

Suitable labels include, by way of illustration and not limitation, enzymes such as alkaline phosphatase, glucose-6-phosphate dehydrogenase ("G6PDH") and horse-radish peroxidase; ribozyme; a substrate for a replicase such as QB replicase; promoters; dyes; fluorescers, such as fluorescein, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}I$, $^{131}I$, $^{14}C$, $^3H$, $^{57}Co$ and $^{75}Se$; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, for example, desirably by visual examination or by electromagnetic radiation, heat, and chemical reagents. The label or other sps members can also be bound to an sbp member, another molecule or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody; a receptor for an antibody; a receptor that is capable of binding to a small molecule conjugated to an antibody; or a ligand analog. Bonding of the label to the sbp member may be accomplished by chemical reactions which result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art.

See for example, Rubenstein, et al, U.S. Pat. No. 3,817,837, incorporated herein by reference. This invention also contemplates having an antibody bound to a first sps member and a detectable label as the second sps member. For example, when the detectable label is bound to a ligand analog, the extent of binding of the antibody to the analog can be measured by detecting the signal produced by the interaction of the sps members.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, preservatives, antimicrobials, or the like.

As mentioned above, one aspect of the present invention is an assay method for measuring the amount of mycophenolic acid in a sample suspected of containing mycophenolic acid and endogenous proteins that bind to the mycophenolic acid. In the method the sample, assay reagents for measuring the amount of the mycophenolic acid, and a releasing agent in an amount effective to release the mycophenolic acid from a complex thereof with endogenous proteins are combined in a medium. The amount of the mycophenolic acid is determined by means of the assay reagents.

The "releasing agent" is any compound capable of releasing MPA from a protein complex thereof. Suitable releasing agents include 8-anilino-1-naphthalene sulfonic acid, anisic acid, clofibric acid (p-chlorophenoxydimethylacetic acid), benzoic acid, 3-(p-hydroxyphenyl)propionic acid, salicylate (salicylic acid), p-methoxysalicyclic acid, and so forth.

It is important in the present invention that the releasing agent not bind to any significant degree to an sbp member or binding partner for MPA used in an assay for MPA. What constitutes a significant degree is dependent on the sensitivity necessary for the assay; the higher the sensitivity required for the assay, the less tolerable is the amount of binding between an sbp member or binding partner for the analyte. By the term "significant degree" is meant that the particular releasing agent not bind to an sbp member or binding partner to an extent that would affect the accuracy or the quantitative or qualitative nature of the assay result. Accordingly, any binding between a particular releasing agent and an sbp member or a binding partner should be preferably less than 1%, more preferably, less than 0.01%, most preferably, 0%. Furthermore, the particular releasing agent selected must have minimal, if any, interference with the binding of sbp members to one another or with the ability of the signal producing system to produce a signal in relation to the presence or amount MPA in a sample.

By the term "effective amount" is meant an amount sufficient to bring about the release of MPA from such complex so that preferably at least about 90%, more preferably, at least about 95%, more preferably, at least 99% and most preferably 100% of the MPA is in a form free of such complex. The effective amount of releasing agent to be used in a particular assay will depend on the nature of the assay and reagents employed therein. Preferably, the effective amount is determined empirically based on the suspected concentration range of MPA in the sample. In general, an effective amount of releasing agent is an excess amount over the suspected amount of MPA. For an assay for MPA, by way of illustration and not limitation, where the expected level of drug in a sample is about 1.5–45 $\mu M$, the effective amount of releasing agent in the assay medium is about 0.1 to about 100 mM, preferably, about 1 to about 25 mM, more preferably, about 2 to 12 mM.

Many of the compounds useful as releasing agents in the present invention are commercially available and/or their synthesis is known in the literature.

The assay for MPA can be performed either without separation (homogeneous) or with separation (heterogeneous) of any of the assay components or products. Homogeneous immunoassays are exemplified by the EMIT® assay products (Behring Diagnostics Inc. formerly Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T. supra. Exemplary of heterogeneous assays are the radioimmunoassay, disclosed in Yalow, et al, *J. Clin. Invest.* 39:1157 (1960). The above disclosures are all incorporated herein by reference. Immunoassays involve the use of immunoassay reagents in the detection of an analyte. Such immunoassay reagents include antibodies, antigens and haptens, and conjugates thereof, either labeled or unlabeled.

The assay is normally carried out in an aqueous buffered medium at a moderate pH, generally that which provides optimum assay sensitivity. The aqueous medium may be solely water or may include some percentage of a cosolvent, for example, from 0.1–40 volume percent of an organic solvent. The pH for the medium will usually be in the range of 4–11, more usually in the range of 5–10, and preferably in the range of 6.5–9.5. The pH will usually be a compromise between optimum binding of the binding members of any specific binding pairs, optimum release of the MPA from a non-specific complex thereof in accordance with the present invention, and the pH optimum for other reagents of the assay such as members of the signal producing system.

Various buffers may be used to achieve the desired pH and maintain the pH during the determination. Illustrative buffers include borate, phosphate, carbonate, tris and barbital. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from 5–45° C., more usually from 15–40° C. Temperatures during measurements will generally range from 10–50° C., more usually from 15–40° C.

The concentration of MPA that may be assayed will generally vary from $10^{-4}$ to $10^{-13}$ M, more usually from $10^{-5}$ to $10^{-7}$ M. Considerations, such as whether the assay is qualitative, semiquantitative or quantitative (relative to the amount of analyte present in the sample), the particular detection technique and the concentration of the analyte will normally determine the concentrations of the various reagents.

The concentrations of the various reagents in the assay medium will generally be determined by the concentration range of interest of MPA. However, the final concentration of each of the reagents will normally be determined empirically to optimize the sensitivity of the assay over the range. That is, a variation in concentration of MPA which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from 30 seconds to 6 hours, more usually from 1 minute to 1 hour.

The following examples further describe the specific embodiments of the invention, and are intended to describe and not to limit the scope of the invention.

In a homogeneous assay after all of the reagents have been combined, the signal is determined and related to the amount of MPA in the sample. For example, in an EMIT assay for MPA, a sample suspected of containing MPA is combined in an aqueous medium either simultaneously or sequentially with an MPA-enzyme conjugate and antibody capable of recognizing MPA and the conjugate. The medium also contains an effective amount of a releasing agent. Generally, a substrate for the enzyme is added which results in the formation of a chromogenic or fluorogenic product upon enzyme catalyzed reaction. Preferred enzymes are glucose-6-phosphate dehydrogenase and alkaline phosphatase. The releasing agent acts to release MPA from any non-specific complex thereof that may be present in the sample. The MPA and the MPA-enzyme conjugate compete for binding sites on the antibody. The enzyme activity in the medium is then determined, usually by spectrophotometric means, and is compared to the enzyme activity determined when calibrators or reference samples are tested in which a known amount of MPA is present. Typically, the calibrators are tested in a manner similar to the testing of the sample suspected of containing MPA. The calibrators will typically contain differing, but known, concentrations of the MPA analyte to be determined. Preferably, the concentration ranges present in the calibrators will span the range of suspected MPA concentrations in the unknown samples.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In a typical competitive assay a support having an antibody for MPA bound thereto is contacted with a medium containing the sample and MPA conjugated to a detectable label such as an enzyme. The medium also contains an effective amount of a releasing agent. MPA in the sample competes with the conjugate for binding to the antibody. After separating the support and the medium, the label activity of the support or the medium is determined by conventional techniques and related to the amount of MPA in the sample.

As mentioned above, the present invention provides certain advantages. Variable recovery of MPA as a function of protein concentration relative to a calibrator matrix is substantially reduced or eliminated. Furthermore, variable recovery of MPA as a function of the presence of co-administered drugs is substantially reduced or eliminated because competition for binding sites on endogenous non-specific binding substances between MPA and other drugs that bind to such substances is reduced or eliminated.

In one MPA assay in accordance with the present invention, antibodies are employed that are capable of binding to MPA and to its esters and metabolites. In another MPA assay in accordance with the present invention, antibodies are used that are capable of distinguishing between MPA and mycophenolate esters, such as MPA-M. In another embodiment of an MPA assay in accordance with the invention, the antibodies employed are able to distinguish between MPA and MPA metabolites, such as MPA-G.

The binding of the antibody to MPA can be detected in numerous ways that are well known in the art. Binding of the antibody and MPA forms an immune complex that can be detected directly or indirectly. The immune complexes are detected directly, for example, when the antibodies employed are conjugated to a label. The immune complex is detected indirectly by examining for the effect of immune complex formation in an assay medium on a signal producing system or by employing a labeled receptor that specifically binds to an antibody of the invention.

Another aspect of the present invention relates to kits useful for conveniently performing an assay for the determination of MPA. A kit in accordance with the present invention comprises in packaged combination a binding partner for MPA and a releasing agent. The kit may further comprise a conjugate of MPA bound to a detectable label.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents. For example, an aqueous solution of the releasing agent can be provided in a separate container. Alternatively, a releasing agent can be included in one of the reagents for conducting an assay. For example, the releasing agent can be included in an aqueous medium containing an antibody reagent; such medium is packaged in a separate container.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages herein are by weight unless otherwise indicated. Temperatures are in degrees Centigrade (° C.).

Example 1

Assay for MPA

The following reagents were prepared:

| # | COMPONENT | % Comp. (by weight) | Comp. by wt./vol. (g/L) (at 20° C.) | COMPONENT SOURCE |
|---|---|---|---|---|
| | REAGENT A | | | |
| 1 | NAD | 2.346 | 23.88 | Boehringer Mannheim |
| 2 | G6P | 0.615 | 6.26 | Calzyme |
| 3 | sodium chloride | 0.491 | 5.00 | Mallinckrodt |
| 4 | MIT | 0.098 | 1.00 | Boehringer Mannheim |
| 5 | Na2 EDTA | 0.036 | 0.37 | Sigma |
| 6 | PLURONIC ® 25R2 | 0.010 | 0.1028 | BASF Chemicals |
| 7 | o-anisic acid | 0.149 | 1.52 | Sigma |
| 8 | BSA | 0.098 | 1.00 | Miles Diagnostics |
| 9 | sodium azide | 0.092 | 0.94 | Amersham USB |
| 10 | Antibody to MPA | 0.001 | 0.0075 | (1) |
| 11 | water | 96.062 | 977.82 | Millipore deionized |
| | | 100.00 | 1017.9 | |
| | pH | 5.6 ± 0.1 | | |
| | REAGENT B | | | |
| 12 | Tris Base | 2.120 | 21.54 | Sigma |
| 13 | Tris HCl | 3.447 | 35.02 | Sigma |
| 14 | BLG | 0.098 | 1.00 | International Enzymes |
| 15 | Na2 EDTA | 0.036 | 0.37 | Sigma |
| 16 | MIT | 0.098 | 1.00 | Boehringer Mannheim |
| 17 | sodium azide | 0.093 | 0.94 | Amersham USB |
| 18 | PLURONIC ® 25R2 | 0.030 | 0.3084 | BASF Chemicals |
| 19 | MPA-G6PDH | 0.00005 | 0.0005 | (2) |
| 20 | Stabilizing antibody | 0.00007 | 0.00075 | (1) |
| 21 | water | 94.077 | 955.92 | Millipore deoinized |
| | | 100.000 | 1016.1 | |
| | pH | 8.15 ± 0.15 | | |

Reagents A and B were prepared as follows.

A 1.028% weight per weight solution of PLURONIC® 25R2 was prepared at 2 to 25° C. for use in both reagents.

Reagent A was prepared by first making an anisic acid solution. Anisic acid was dissolved in 1N NaOH in an amount equal to 25 mL per 1.52 grams of anisic acid. In a separate container was weighed 70% of the final weight of deionized water, to which was added components 1 through 5 inclusive and also component 6 using the prepared solution of PLURONIC® 25R2 at 10 mL thereof per 1017.9 g (or 1.0 liter) of final solution. This solution was stirred and the anisic acid solution was added. If necessary, the pH of the preparation was adjusted within the range of 5.50 to 5.70 with 6 N NaOH. Next, components 8 and 9 were added and the solution was stirred. If necessary, the pH was adjusted to the above range. The solution was then brought to the final weight with deionized water and was filtered through a 0.2 micron filter. Final pH was 5.50 to 5.70. The resulting solution was designated the A diluent. Reagent A was completed by adding antibody, i.e., component 10, to the A diluent to a final antibody concentration of 7.5 mg/L (or 7.5 μg/mL).

It is noted that Reagent A contained BSA, which like human serum albumin binds MPA. However, the BSA was found to be a preferred stabilizer of Reagent A over certain other proteins that were evaluated, and thus was included in Reagent A for this reason. Any releasing agent for MPA, therefore, would be formulated to overcome this effect of BSA as well as any binding from the sample being analyzed. The above formulation had greater than a 500-molar excess of o-anisic acid to BSA in Reagent A. This concentration of o-anisic acid was found to be more than sufficient to release all MPA in the system and keep it displaced.

For Reagent B deionized water was weighed in an amount equal to 80% of the final weight. To this water was added with stirring components 12 through 17 inclusive as well as component 18, using 30 mL of PLURONIC® 25R2 solution per 1016.1 g (or 1.0 liter) of final solution. The solution was brought to the final weight with deionized water, pH in the range of 8.0 to 8.3, and was filtered through 0.2 micron filter. The solution at this point was designated the B diluent, which was used to make Reagent B by addition of relatively negligible volumes or weights of components 19 and 20. For example 0.37 mL of stabilizing antibody at 20.6 mg/mL and 6.1 mL of conjugate at 0.8 mg/mL were added to 10 L (or 10.18 kg) of Reagent B. The stabilizing antibody, component 20, was added to a final concentration of 0.75 mg/L (or 0.75 µg/mL). The conjugate, component 19, was added to achieve a rate of 300±10 mA/min; rate is defined as the change in absorbance at 340 nm per minute of reaction time and is usually expressed as mA/min.

Rates were determined on a Cobas Mira Plus® instrument (Roche Diagnostics Systems, Inc., Branchburg, N.J.). The temperature was kept at 37° C. for the entire assay. Timings were carried out in cycles with each cycle being 25 seconds. In cycle 1, the first cycle, 75 µL of water and 3 µL of a sample were mixed with 155 µL of A diluent in a 0.6 cm path length cuvette. This mixture was incubated until the addition of Reagent B in cycle 7. To establish the conjugate rate, the sample used did not contain any MPA. In cycle 7, seventy-five µL of Reagent B followed by 20 µL of water was then added to the cuvette, mixed, and incubated until the end of cycle 25 at which time the assay was finished. During the assay, absorbance readings at 340 nm were made at the end of every cycle. A best linear fit was then made using only the 12 consecutive absorbance readings of cycles 14 through 25 versus time in minutes. The slope of this line was the rate.

Reagent A preparations were then made by adding antibody at different levels to the A diluent. These titration levels were then run with Reagent B and calibrators with different levels of MPA (e.g., 0, 0.5, 2.0, 5.0, 10.0, and 15.0 µg/mL). The level of antibody giving the maximum rate separations between the two low end calibrators and between the two high end calibrators was then used to formulate the final Reagent A.

Once Reagent A and B were prepared they were used along with calibrators to determine unknown concentrations of MPA.

To determine an unknown MPA concentration, calibrators were run with Reagents A and B, and rates were determined for each as previously described, except that Reagent A containing antibody was substituted for the A diluent. Duplicate rates were typically determined for each calibrator and averaged. The calibration curve parameters were calculated using the MPA concentrations, average calibrator rates and an appropriate mathematical model such as a logit/log 4 model fit. The fit can be made on line by the analyzer or by appropriate computer programs which optimize the parameters Ro, Kc, a and b in the following equation:

$$R = Ro + \frac{Kc}{1 + \exp[-(a + b \cdot \ln C)]}$$

where

Ro, Kc, a, b are curve parameters
C is the MPA concentration
R is the rate observed with the MPA concentration Solving this equation for C allowed the unknown MPA concentration to be determined from its rate, R, and the curve parameters as:

$$C = \exp[[a + \ln[Kc/(R - Ro) - 1.0]]/-b]$$

The results are summarized as follows:

The effectiveness of the formulation with o-anisic acid was evaluated by measuring the agreement between the quantitation of a 10 µg/mL MPA spike in a normal human plasma pool (NHP) and the quantitation of a similar spike into Dulbecco's phosphate buffered saline (PBS), purchased from BioWhittaker, Walkersville, Md. For both NHP and PBS, two separate spikes were made. PBS contained 0.2 g/L KCl, 0.2 g/L $KH_2PO_4$, 2.16 g/L $Na_2HPO_4 \cdot 7\ H_2O$, and 8.0 g/L NaCl at a final pH 6.4 to 7.6. The PBS had no protein and thus no protein binding of MPA can occur. Calibrators were NHP with 7 levels of MPA at 0, 0.3, 0.5, 2.5, 5, 10, and 20 µg/mL. The NHP and PBS spikes quantitated nearly the same, giving respective averages of 10.2 and 10.4 µg/mL MPA (pooled standard deviation (sd)=0.4 µg/mL). These results indicate that the method was measuring total MPA and was not affected by normal serum albumin binding of MPA.

Example 2

Releasing Agents in an MPA Assay

In this example four agents, o-anisic acid (o-M), its meta (m-AA) and para (p-AA) isomers, and 8-anilino-1-naphthalene sulfonic acid (ANS) were compared. All the anisic acids were purchased from Sigma Chemical Company, St. Louis, Mo.; the ANS was obtained from Calbiochem, La Jolla, Calif.

In these experiments, the diluent for Reagent A (Rgt A) was made somewhat differently than that in Example 1. However, the composition was the same, except for component 7 (releasing agent, o-anisic acid) and component 10 (concentration of MPA antibody). Five diluents were prepared, four with one of each of the above agents and one control with no agent. First, a 2× solution was made in the manner described in Example 1 but which had only components 1 through 5 and 9 at twice the amounts listed. Next, for three of the diluents, each of the three anisic acid isomers was weighed to achieve a final molarity of 12.5 mM and predissolved in one quarter the final volume of water and a minimum amount of 6 N NaOH (approximately 6 drops per 0.2 grams anisic acid). For the fourth diluent, the agent, ANS, was weighed to give a 0.25 mM final concentration and added to one quarter the final volume of water. The fifth diluent, the control, had no releasing agent. To make each of these five diluents, the appropriate amounts of the 2× solution, the 1× amount of BSA, component 8, and the 1x amount of the PLURONIC® 25R solution, component 6, were combined. Four of these then received the appropriate agent. All were mixed well. Where necessary, pH adjustments were made as described previously and each preparation was brought to the final volume with deionized water to achieve 1× concentrations of components. Each of these A diluents was then filtered through a 0.2 micron filter. Final pH measurements on each were all between 5.5 to 5.7. For each of these five A diluents, a corresponding Reagent A was made by adding antibody to MPA for a final concentration of 6.5 μg/mL. Reagent B (Rgt B) was prepared as described in Example 1 except that component 20 was omitted and 0.1% BSA (Miles Diagnostics, Kankakee, Ill.) was substituted for BLG.

It should be noted that the concentration of ANS in Reagent A was limited due to its contribution to background absorbance. Higher concentrations of ANS created an offscale absorbance reading, preventing the collection of rate data. It should be further noted that all of the Reagent A preparations were visually colorless except for the Reagent A with ANS which had a tannish yellow color.

In a total of two runs the effects of each of the four agents relative to a control of no agent were examined with respect to (1) background absorbance at 340 nm, (2) the rate of a negative MPA sample, (3) the rate span between 0 and 10 μg/mL MPA, and (4) the closeness of rate matching of a 10 μg/mL MPA spike in NHP and in buffer. Both runs included the control Reagent A. The first run evaluated Reagent A with ANS while the second run evaluated Reagent A preparations containing the structural isomers of anisic acid.

MPA was spiked into NHP and buffer (Buff) to achieve a final concentration of 10 μg/mL MPA. Buffer in this example was 50 mM MES (2-[N-morpholino]ethanesulfonic acid, obtained from Sigma Chemical Company) with 0.1% (weight/volume) sodium azide, pH 7.1. As with PBS, this buffer has no protein and thus no protein binding of MPA can occur.

In both runs, the background absorbance at 340 nm for each Reagent A was measured in duplicate on a 230-μL combination of 3 μL negative NHP, 72 μL of deionized water, and 155 μL Reagent A. The cell path length was 0.6 cm. The average $A_{340}$ (A=absorbance) values are found in Column C of Table 1. Duplicate rates were determined on the spiked and unspiked NHP and buffer similar to Example 1. The only changes from Example 1 for rate determinations were in the protocol timings. These changes are noted as follows. Reagent B and water were added in cycle 4. The analysis was finished at the end of cycle 15. Rates were determined using the 5 absorbance readings of cycles 11 through 15.

Averages of these rates are summarized in Table 1 in columns E through H.

The effectiveness of the releasing agent was determined by subtracting the spiked NHP rate from the spiked buffer rate (column H–column F). The closer this value was to zero, the better the releasing effect.

All four agents showed some effect on either the negative rate and/or rate span as compared to control values. This indicated that the agents are having effects other than reducing the matrix effect of the NHP. The anisic acids had a marked increase in negative rate over the control whereas ANS has little or no effect. ANS had the largest increase in rate span.

Example 3

Effect of o-Anisic Acid and ANS on MPA Rates in the Presence of Co-administered Drugs and Salicylic Acid In a separate study, the ability of o-anisic acid or ANS to eliminate the effect of salicylate on rates of MPA plasma spikes was compared. Three sets of antibody reagents (Reagent A) were prepared to the basic formulation described in Example 2 above. In one reagent, no releasing agent was added; in another reagent, o-anisic acid was added at 12.5 mM, and in a third reagent ANS was added at 0.27 mM. A common Reagent B was prepared as described in Example 2.

Rates for four levels of MPA spikes into plasma and a plasma control were measured with each reagent set. A similar set of plasma spikes was prepared with plasma containing non-interfering co-administered drugs, and another set of plasma spikes was prepared containing non-interfering drugs plus salicylate. Concentrations of the non-interfering drugs in μg/mL were as follows: ampicillin, 36; cefaclor, 26; chloramphenicol, 64; trimethoprim, 2; albuterol, 7; isoproterenol, 18; metoprolol, 77; diltiazem, 28; nifedipine, 22; verapamil, 12; fenoprofen, 16; indomethacin, 36; ketoconazole, 75; miconazole, 106; isoniazid, 120; 5-fluorouracil, 23; griseofulvin, 10; methotrexate, 2; diphenhydramine, 93; dl-ephedrine, 103; phenylephrine, 76; disopyramide, 52; procainamide, 64; metoclopramide, 5; niacin, 25; niacinamide, 47; acetaminophen, 87; and lidocaine, 43. Salicylate was present at 659 μg/mL.

Rates were determined as described in Example 2 above with the exception of the absorbance read window, which was extended to cycle 20 where the assay was ended. Rates

TABLE 1

| RUN # | A Agent | B CONC. in Rgt A mM | C A 340 nm | D Δ A = agent · control Δ A 340 nm | E NHP with 0 μg/mL MPA Rate mA/min | F NHP with 10 μg/mL MPA Rate mA/min | G Buff with 0 μg/mL MPA Rate mA/min | H Buff with 10 μg/mL MPA Rate mA/min | I (H − G) Buff Rate Span mA/min | J (H − F) Buff-NHP Rate Diff. mA/min |
|---|---|---|---|---|---|---|---|---|---|---|
| 1 | NONE (control) | 0 | 0.457 | — | 161.0 | 240.5 | 159.4 | 250.8 | 91.4 | 10.3 |
|   | ANS | 0.25 | 0.779 | 0.322 | 158.2 | 274.2 | 156.0 | 276.2 | 120.2 | 2.0 |
| 2 | NONE (control) | 0 | 0.486 | — | 159.1 | 238.7 | 159.5 | 250.6 | 91.1 | 11.9 |
|   | o-AA | 12.5 | 0.490 | 0.004 | 169.5 | 276.9 | 168.2 | 277.5 | 109.3 | 0.6 |
|   | m-AA | 12.5 | 0.494 | 0.008 | 188.1 | 280.3 | 189.4 | 279.7 | 90.3 | −0.6 |
|   | p-AA | 12.5 | 0.494 | 0.008 | 182.7 | 280.4 | 182.3 | 278.3 | 96.0 | −2.1 | were determined using the 10 consecutive absorbance readings of cycles 11 through 20. The results are summarized in Table 2.

TABLE 2

|  | Antibody Reagent Only | Antibody Reagent + ANS | Antibody Reagent + o-Anisic Acid |
|---|---|---|---|
| MPA + MeOH* | | | |
| 0 μg/mL | 149 | 147 | 161 |
| 0.5 μg/mL | 155 | 157 | 171 |
| 2.5 μg/mL | 181 | 212 | 210 |
| 5 μg/mL | 201 | 237 | 234 |
| 15 μg/mL | 240 | 261 | 264 |
| MPA + NI** | | | |
| 0 μg/mL | 149 | 147 | 161 |
| 0.5 μg/mL | 158 | 162 | 173 |
| 2.5 μg/mL | 183 | 213 | 211 |
| 5 μg/mL | 204 | 236 | 234 |
| 15 μg/mL | 242 | 261 | 263 |
| MPA + NI + Salicylate** | | | |
| 0 μg/mL | 149 | 149 | 161 |
| 0.5 μg/mL | 157 | 159 | 171 |
| 2.5 μg/mL | 190 | 212 | 211 |
| 5 μg/mL | 210 | 237 | 234 |
| 15 μg/mL | 250 | 261 | 263 |

*MeOH = plasma spiked with methanol as control for NI spike.
**NI = plasma contains spikes of non-interfering co-administered drugs in addition to MPA.

In summary, salicylate increased rates of MPA in normal human plasma in the absence of releasing agents, which could result in inaccurate quantitation of MPA in an assay. The presence of a releasing agent in the antibody reagent eliminated this potential problem in an assay for MPA.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art are intended to be within the scope of the following claims.

What is claimed is:

1. An assay method for measuring the amount of mycophenolic acid in a sample suspected of containing said mycophenolic acid and endogenous proteins that form a complex with said mycophenolic acid, said method comprising:
   (a) combining in an aqueous medium (i) said sample, (ii) at least one assay reagent comprising a signal producing system which produces a detectable signal depending on the amount of said mycophenolic acid in the sample, wherein the signal producing system comprises an exogenous binding partner that specifically binds to mycophenolic acid, and (iii) a releasing agent in an amount effective to release said mycophenolic acid from the complex thereof with said endogenous proteins to provide at least about 90% of said mycophenolic acid in a form free of such complex, and
   (b) determining the amount of said mycophenolic acid by measuring the signal produced by the signal producing system.

2. The assay method of claim 1 wherein said releasing agent is selected from the group consisting of anisic acid and 8-anilino-1-naphthalene sulfonic acid.

3. The assay method of claim 1 wherein said signal producing system comprises an enzyme.

4. A method for determining the amount of mycophenolic acid in a sample suspected of containing said mycophenolic acid complexed with endogenous proteins that bind said mycophenolic acid said method comprising
   (a) providing in combination in an assay medium said sample, an exogenous binding partner for said mycophenolic acid, wherein said binding partner comprises a molecule that specifically binds to said mycophenolic acid, a releasing agent in an amount effective to release said mycophenolic acid from a complex thereof with endogenous proteins to provide at least about 90% of said mycophenolic acid in a form free of such complex and (b) detecting the binding of said binding partner to said mycophenolic acid.

5. The assay method of claim 4 wherein said releasing agent is selected from the group consisting of anisic acid and 8-anilino-1-naphthalene sulfonic acid.

6. The assay method of claim 4 wherein the assay medium further comprises at least one reagent comprising a label which produces a detectable signal depending on the amount of mycophenolic acid in the sample.

7. The method of claim 4, wherein step (a) further comprises contacting said sample with a labeled analog of mycophenolic acid.

8. The method of claim 4, wherein said binding partner is bound to a support.

9. The method of claim 4, wherein said binding partner is an antibody.

10. A method for measuring the amount of mycophenolic acid in a sample suspected of containing said mycophenolic acid and endogenous proteins that complex with said mycophenolic acid, said method comprising
    (a) combining in an aqueous medium:
       (i) said sample,
       (ii) mycophenolic acid conjugated to a label having a detectable activity, and
       (iii) an antibody capable of binding to mycophenolic acid,
    (b) providing in said medium a releasing agent in an amount effective to release said mycophenolic acid from the complex with said endogenous proteins to provide at least about 90% of said mycophenolic acid in a form free of such complex, and
    (c) determining an increase or decrease in the activity of said label in response to the amount of mycophenolic acid in the sample.

11. The method of claim 10 wherein said releasing agent is an anisic acid or 8-anilino-1-naphthalene sulfonic acid.

12. The method of claim 10 wherein said detectable label is an enzyme and said determining step comprises measuring the activity of said enzyme.

13. The method of claim 10 which further comprises providing a substrate for said enzyme wherein the enzyme reacts with the substrate.

14. The method of claim 12 wherein said enzyme is selected from the group consisting of glucose-6-phosphate dehydrogenase and alkaline phosphatase.

15. The method of claim 10 wherein said releasing agent is o-methoxybenzoic acid.

16. The method of claim 10 wherein said antibody is a monoclonal antibody.

17. The method of claim 10 wherein said antibody is bound to a support.

18. The method of claim 10 wherein said antibody preferentially binds to mycophenolic acid relative to an ester thereof.

19. The method of claim 10 wherein said antibody preferentially binds to mycophenolic acid relative to a metabolite of mycophenolic acid.

20. The method of claim 10 which is a homogeneous immunoassay and further comprises the step of (c) comparing said activity to the activity measured with a sample containing a known amount of said mycophenolic acid.

21. A kit for determining the amount of mycophenolic acid in a sample suspected of containing said mycophenolic acid and endogenous proteins that bind to said mycophenolic acid comprising in packaged combination:

(a) an antibody capable of binding to said mycophenolic acid, (b) a compound comprising mycophenolic acid bound to a detectable label, and (c) a releasing agent in an amount effective to provide at least about 90% of said mycophenolic acid in a form free of said proteins.

22. The kit of claim 21 wherein said antibody is a monoclonal antibody.

23. The kit of claim 21 wherein said antibody is bound to a support.

24. The kit of claim 21 wherein said antibody preferentially binds to mycophenolic acid relative to an ester thereof.

25. The kit of claim 21 wherein said antibody preferentially binds to mycophenolic acid relative to a metabolite of mycophenolic acid.

26. A method for releasing mycophenolic acid present in a medium suspected of containing said mycophenolic acid in a complex with endogenous proteins that bind to said mycophenolic acid, said method comprising combining:

the medium with a releasing agent in an amount sufficient to provide at least about 90% of said mycophenolic acid in a form free of said complex.

27. The method of claim 26 wherein said releasing agent is selected from the group consisting of anisic acid and 8-anilino-1-naphthalene sulfonic acid.

28. The assay method of claim 1 wherein the signal producing system comprises a first member of a specific binding pair coupled to a label wherein the first member of the specific binding pair either binds to said mycophenolic acid or competes with said mycophenolic acid for binding with a second member of the specific binding pair and wherein the label produces a detectable signal depending on the amount of mycophenolic acid in the sample.

* * * * *